United States Patent

Ree

Patent Number: 5,795,242
Date of Patent: Aug. 18, 1998

[54] HEALTHY GOLF CLUB GRIP

[76] Inventor: Sook H. Ree, 2 Edgewood La., Roslyn, N.Y. 11576

[21] Appl. No.: 800,954

[22] Filed: Feb. 18, 1997

[51] Int. Cl.$^6$ .................................................. A63B 49/08
[52] U.S. Cl. ........................................................... 473/303
[58] Field of Search ................................ 473/300, 301, 473/302, 303, 549, 550; 601/15, 19, 40

[56] References Cited

U.S. PATENT DOCUMENTS

| | | | |
|---|---|---|---|
| D. 363,963 | 11/1995 | Boone et al. | D21/222 |
| D. 365,131 | 12/1995 | Edwards et al. | D21/222 |
| 2,046,164 | 6/1936 | Herkner | 473/302 |
| 2,446,622 | 8/1948 | Turner | 473/302 |
| 3,888,241 | 6/1975 | Fischer | 601/19 |
| 4,552,713 | 11/1985 | Cavicchioli | 264/162 |
| 4,919,420 | 4/1990 | Sato . | |
| 5,139,014 | 8/1992 | Chang | 601/19 |
| 5,234,740 | 8/1993 | Reeves et al. | 473/303 |
| 5,248,141 | 9/1993 | Kelly . | |
| 5,261,665 | 11/1993 | Downey . | |
| 5,299,802 | 4/1994 | Bouchet-Lassale . | |
| 5,382,222 | 1/1995 | Yih-Jong | 601/15 |
| 5,575,760 | 11/1996 | Masuda | 601/19 |
| 5,634,859 | 6/1997 | Nesbitt | 473/302 |

Primary Examiner—Steven B. Wong
Attorney, Agent, or Firm—Richard L. Miller, P.E

[57] ABSTRACT

A healthy golf club grip adaptable to a shaft of a golf club. The grip includes an elongated, slender, and slightly downwardly tapering cylindrically-shaped core, and a cover layer of resilient material. The elongated, slender, and slightly downwardly tapering cylindrically-shaped core has a wide and circular-shaped proximal end, a narrow and circular-shaped socket distal end that is adapted to receive the shaft of the golf club, and an outer longitudinal surface that extends from the wide and circular-shaped proximal end of the elongated, slender, and slightly downwardly tapering cylindrically-shaped core to the narrow and circular-shaped socket distal end of the elongated, slender, and slightly downwardly tapering cylindrically-shaped core. The cover layer of resilient material covers the outer longitudinal surface of the elongated, slender, and slightly downwardly tapering cylindrically-shaped core in its entirety. And, the cover layer of resilient material has a plurality of hemispherically-shaped projections that extend outwardly therefrom, in close proximity to each other, and cover the cover layer of resilient material in its entirety.

3 Claims, 1 Drawing Sheet

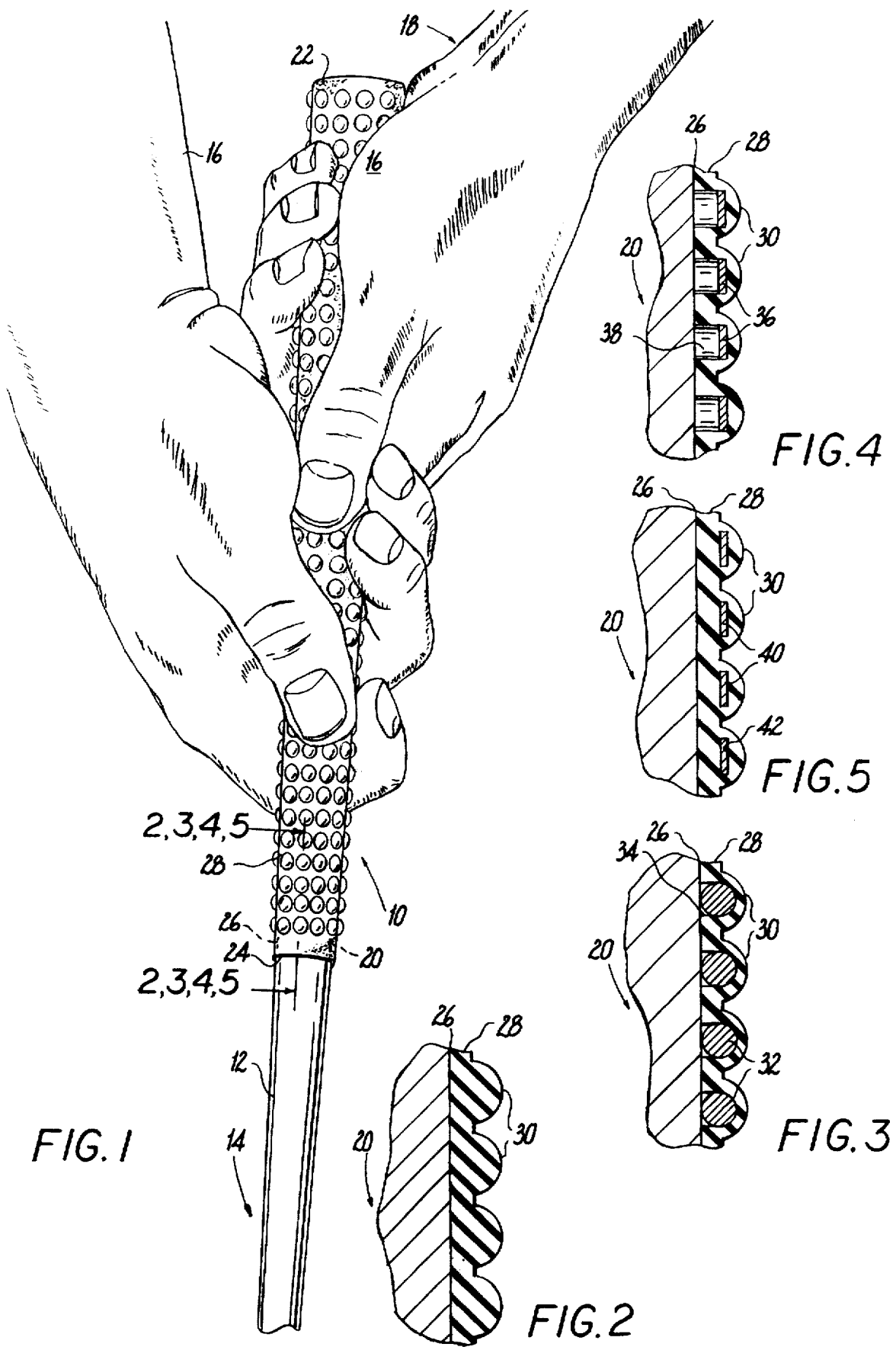

5,795,242

1

HEALTHY GOLF CLUB GRIP

BACKGROUND OF THE INVENTION

The present invention relates to a golf club grip. More particularly, the present invention relates to a healthy golf club grip that prevents irritation to the palms of a golfer not wearing gloves while providing acupressure thereto.

Grips having a wide variety of different construction have been fabricated for use as golf clubs over the years. The shaft of a golf club is an elongated, narrow, cylindrical surface which may be formed of solid wood, a solid metal rod, or hollow metal tubing which may be a composite formed of carbon graphite or steel. The extremity of the shaft of the golf club which is held by a golfer is typically quite narrow, usually no more than about five eights of an inch in diameter at the most. The golf club shaft is normally quite smooth, so that a grip of some type is essential to allow the golfer to control the swing of the club.

Golf club grips having a wide variety of configurations and structure have been employed over the years. Some golf club grips are formed by strips of some outer material, such as leather, overwound about some packing material to extend along the upper end of the shaft of the club for a distance of about ten to twelve inches. Other golf club grips are formed of a single material secured about the upper extremity of the shaft of the golf club. Still other grips are formed of several different materials, arranged in layers on the end of the shaft of the golf club.

The construction and physical characteristics of a golf club grip are extremely important, since minuscule variations in the physical characteristics of a golf club grip will produce very pronounced effects upon the accuracy of golf shots.

Numerous innovations for golf club grips have been provided in the prior art that will be described. Even though these innovations may be suitable for the specific individual purposes to which they address, however, they differ from the present invention in that they do not teach a healthy golf club grip that includes an elongated, slender, and slightly downwardly tapering cylindrically-shaped core, and a cover layer of resilient material, wherein the elongated, slender, and slightly downwardly tapering cylindrically-shaped core has a wide and circular-shaped proximal end, a narrow and circular-shaped socket distal end that is adapted to receive the shaft of the golf club, and an outer longitudinal surface that extends from the wide and circular-shaped proximal end of the elongated, slender, and slightly downwardly tapering cylindrically-shaped core to the narrow and circular-shaped socket distal end of the elongated, slender, and slightly downwardly tapering cylindrically-shaped core, wherein the cover layer of resilient material covers the outer longitudinal surface of the elongated, slender, and slightly downwardly tapering cylindrically-shaped core in its entirety, and wherein the cover layer of resilient material has a plurality of hemispherically-shaped projections that extend outwardly therefrom, in close proximity to each other, and cover the cover layer of resilient material in its entirety.

FOR EXAMPLE, U.S. Pat. No. Des. 363,963 to Boone et al. teaches the ornamental design for the golf club grip.

ANOTHER EXAMPLE, U.S. Pat. No. Des. 365,131 to Edwards et al. teaches the ornamental design for the golf club grip.

STILL ANOTHER EXAMPLE, U.S. Pat. No. 4,552,713 to Cavicchioli teaches a handgrip, such as a golf club grip, having improved non-slip features which is formed from a silicone rubber composition. The silicone rubber composition comprises an organopolysiloxane gum, a silica filler material, as organosilicone processing aid, a texturizing material, and a quantity of hollow spheres. The texturizing material and spheres are first blended into the composition while heating the composition. The rubber composition is then placed in a suitable mold and cured with a peroxide catalyst to form the handgrip. The external surface of the cured handgrip is buffed to fracture the hollow spheres nearest the surface and improve the non-slip character of the handgrip.

YET ANOTHER EXAMPLE, U.S. Pat. No. 4,919,420 to Sato teaches a grip of a golf club which prevents slipping when the grip is grasped by a hand opposite to a whip hand, by applying an area having a plurality of projections to the area of the grip corresponding to the respective bases of the middle finger, the ring finger and the little finger of the palm of the hand opposite to the whip hand and to the palm located on the extension of the neighborhood of the base of the little finger of the palm. Also, there is an area where a plurality of projections or dents are formed being separated independently one by one. Accordingly, when the whole of the element body of the grip is ground from the surface in a uniform depth, the fiber is exposed in the area having a plurality of plane portions and the fiber is not exposed in the area having a plurality of jogs. In this area where the fiber is exposed, a moderate non-slip effect is obtainable and soft grip feeling is presented.

STILL YET ANOTHER EXAMPLE, U.S. Pat. No. 5,248,141 to Kelly teaches a grip for use on the extending end of the shaft of a golf club which is provided with an especially configured array of longitudinally extending grooves which are in direct opposition to the rotation of the golf club about the longitudinal axis of the golf club shaft to resist twisting of the golf club in the golfer's hand resulting from mishitting of a golf ball in an off center location toward the toe or heel of the golf club head. Three sets of longitudinally extending grooves are provided in the portions of the grip gripped by the golfer's left and right hands for the purpose of equalizing the static friction exertion capabilities of those portions of the grip. A first plurality of grooves extends longitudinally more than half the length of the grip. A second plurality of grooves extends longitudinally a distance less than the extending distance of the first plurality of grooves. A third plurality of grooves extends longitudinally from points spaced from the lower ends of the second plurality of grooves to a distance which is between ⅔ and ¾ of the length of the grip. The grip may have a visual indicator by which the rotational position of the golf club when being held in a golfer's hands can be determined by visual alignment of the grip with the golfer's hands.

YET STILL ANOTHER EXAMPLE, U.S. Pat. No. 5,261,665 to Downey teaches a golf club grip formed of a hollow, inner socket and an outer jacket produced from different charges of thermoplastic rubber. The socket and jacket differ in stiffness characteristics, colors, or both stiffness and color. The outer jacket is molded onto the socket and bonded thereto throughout the surfaces of contact therebetween. The torsional stress on the jacket is transmitted to and resisted by the inner socket through the bonding that occurs throughout the interface between the jacket and the socket. Preferably, the socket has an inner socket core portion with a plurality of radially projecting protrusions. The structure of the jacket laterally surrounds the protrusions so that the outermost surfaces of the protrusions are exposed. The golf club grip is produced from a pair of identical mounting cores which are rotated between a pair of molding dies. The sockets are first produced on one mounting core in a first die, and the first mounting core with the socket thereon is cyclically moved into the second die. While the jacket of the golf club grip of the invention is being molded onto the socket just produced in the first die, a new socket is concurrently produced on the second mounting core, which has been moved into the first die.

FINALLY, STILL YET ANOTHER EXAMPLE, U.S. Pat. No. 5,299,802 to Bouchet-Lassale teaches a removable grip adapted to be fixed on the existing conventional grip of a golf club that is provided with hollows and protuberances enabling the player to adopt automatically a correct position of the hands on the grip.

It is apparent that numerous innovations for golf club grips have been provided in the prior art that are adapted to be used. Furthermore, even though these innovations may be suitable for the specific individual purposes to which they address, however, they would not be suitable for the purposes of the present invention as heretofore described.

SUMMARY OF THE INVENTION

ACCORDINGLY, AN OBJECT of the present invention is to provide a healthy golf club grip that avoids the disadvantages of the prior art.

ANOTHER OBJECT of the present invention is to provide a healthy golf club grip that is simple and inexpensive to manufacture.

STILL ANOTHER OBJECT of the present invention is to provide a healthy golf club grip that is simple to use.

YET ANOTHER OBJECT of the present invention is to provide a healthy golf club grip that eliminates irritation on the palms of the hands of the golf when golf gloves are not used.

STILL YET ANOTHER OBJECT of the present invention is to provide a healthy golf club grip that provides more efficient stimulation to the acupressure points of the hands.

YET STILL ANOTHER OBJECT of the present invention is to provide a healthy golf club grip that is adaptable to a shaft of a golf club.

BRIEFLY STATED, STILL YET ANOTHER OBJECT of the present invention is to provide a healthy golf club grip that includes an elongated, slender, and slightly downwardly tapering cylindrically-shaped core, and a cover layer of resilient material.

YET STILL ANOTHER OBJECT of the present invention is to provide a healthy golf club grip wherein the elongated, slender, and slightly downwardly tapering cylindrically-shaped core has a wide and circular-shaped proximal end, a narrow and circular-shaped socket distal end that is adapted to receive the shaft of the golf club, and an outer longitudinal surface that extends from the wide and circular-shaped proximal end of the elongated, slender, and slightly downwardly tapering cylindrically-shaped core to the narrow and circular-shaped socket distal end of the elongated, slender, and slightly downwardly tapering cylindrically-shaped core.

STILL YET ANOTHER OBJECT of the present invention is to provide a healthy golf club grip wherein the cover layer of resilient material covers the outer longitudinal surface of the elongated, slender, and slightly downwardly tapering cylindrically-shaped core in its entirety.

YET STILL ANOTHER OBJECT of the present invention is to provide a healthy golf club grip wherein the cover layer of resilient material has a plurality of hemispherically-shaped projections that extend outwardly therefrom, in close proximity to each other, and cover the cover layer of resilient material in its entirety.

STILL YET ANOTHER OBJECT of the present invention is to provide a healthy golf club grip wherein the cover layer of resilient material is one of rubber and fiber material.

YET STILL ANOTHER OBJECT of the present invention is to provide a healthy golf club grip wherein each projection of the plurality of hemispherically-shaped projections on the cover layer of resilient material has a radius of curvature of 5 mm.

STILL YET ANOTHER OBJECT of the present invention is to provide a healthy golf club grip that further includes a plurality of spherically-shaped permanent magnets, each of which is disposed in, and does not fill, a void in each projection of the plurality of hemispherically-shaped projections on the cover layer of resilient material.

YET STILL ANOTHER OBJECT of the present invention is to provide a healthy golf club grip wherein each magnet of the plurality of spherically-shaped permanent magnets contacts the outer longitudinal surface of the elongated, slender, and slightly downwardly tapering cylindrically-shaped core.

STILL YET ANOTHER OBJECT of the present invention is to provide a healthy golf club grip wherein each magnet of the plurality of spherically-shaped magnets has a diameter of 1 mm.

YET STILL ANOTHER OBJECT of the present invention is to provide a healthy golf club grip that further includes a plurality of square-parallelepiped-shaped permanent magnets, each of which is disposed in, and does not fill, a void in each projection of the plurality of hemispherically-shaped projections on the cover layer of resilient material.

STILL YET ANOTHER OBJECT of the present invention is to provide a healthy golf club grip wherein each magnet of the plurality of square-parallelepiped-shaped permanent magnets does not contact the outer longitudinal surface of the elongated, slender, and slightly downwardly tapering cylindrically-shaped core.

YET STILL ANOTHER OBJECT of the present invention is to provide a healthy golf club grip that further includes a plurality of square-parallelepiped-shaped permanent magnets, each of which fills a void in each projection of the plurality of hemispherically-shaped projections on the cover layer of resilient material.

FINALLY, STILL YET ANOTHER OBJECT of the present invention is to provide a healthy golf club grip wherein each magnet of the plurality of square-parallelepiped-shaped permanent magnets does not contact the outer longitudinal surface of the elongated, slender, and slightly downwardly tapering cylindrically-shaped core.

The novel features which are considered characteristic of the present invention are set forth in the appended claims. The invention itself, however, both as to its construction and its method of operation, together with additional objects and advantages thereof, will be best understood from the following description of the specific embodiments when read and understood in connection with the accompanying drawing.

BRIEF DESCRIPTION OF THE DRAWING

The figures on the drawing are briefly described as follows:

FIG. 1 is a diagrammatic perspective view of the present invention in use;

FIG. 2 is an enlarged cross sectional view taken on line 2—2 of FIG. 1, illustrating the cover layer of the present invention without magnets therein;

FIG. 3 is an enlarged cross sectional view taken on line 3—3 of FIG. 1, illustrating a first alternate embodiment of the cover layer of the present invention with spherically-shaped magnets sitting in voids therein;

FIG. 4 is an enlarged cross sectional view taken on line 4—4 of FIG. 1, illustrating a second alternate embodiment of the cover layer of the present invention with square-parallelepiped-shaped magnets sitting in voids therein; and FIG. 5 is an enlarged cross sectional view taken on line 5—5 of FIG. 1, illustrating a third alternate embodiment of the cover layer of the present invention with square-parallelepiped-shaped magnets filling voids therein.

LIST OF REFERENCE NUMERALS UTILIZED IN THE DRAWING 10 healthy golf club grip of the present invention
12 golf club shaft
14 golf club
16 golfer hands
18 golfer
20 elongated, slender, and slightly downwardly tapering cylindrically-shaped core
22 core wide and circular-shaped proximal end
24 core narrow and circular-shaped socket distal end
26 core outer longitudinal surface
28 cover layer of resilient material
30 cover layer plurality of hemispherically-shaped projections
32 cover layer plurality of spherically-shaped permanent magnets
34 cover layer void
36 cover layer plurality of square-parallelepiped-shaped permanent magnets
38 cover layer void
40 cover layer plurality of square-parallelepiped-shaped permanent magnets
42 cover layer void

DETAILED DESCRIPTION OF THE PREFERRED EMBODIMENT

Referring now to the figures in which like numerals indicate like parts, and particularly to FIG. 1, which is a diagrammatic perspective view of the present invention in use, the healthy golf club grip of the present invention is shown generally at 10 attached to a golf club shaft 12 of a golf club 14 and being gripped by golfer hands 16 of a golfer 18.

The healthy golf club grip 10 includes an elongated, slender, and slightly downwardly tapering cylindrically-shaped core 20 that has a core wide and circular-shaped proximal end 22, a core narrow and circular-shaped socket distal end 24 adapted to receive the golf club shaft 12 of the golf club 14, and a core outer longitudinal surface 26 that extends from the core wide and circular-shaped proximal end 22 of the elongated, slender, and slightly downwardly tapering cylindrically-shaped core 20 to the core narrow and circular-shaped socket distal end 24 of the elongated, slender, and slightly downwardly tapering cylindrically-shaped core 20.

The healthy golf club grip 10 further includes a cover layer of resilient material 28 that covers the core outer longitudinal surface 26 of the elongated, slender, and slightly downwardly tapering cylindrically-shaped core 20 in its entirety, and is preferably rubber or a fiber material.

The configuration of the cover layer of resilient material 28 can best be seen in FIG. 2, which is an enlarged cross sectional view taken on line 2—2 of FIG. 1, illustrating the cover layer of the present invention without magnets therein, and as such will be discussed with reference thereto.

The cover layer of resilient material 28 comprises a cover layer plurality of hemispherically-shaped projections 30 that extend outwardly therefrom, in close proximity to each other, and covering the cover layer of resilient material 28 in its entirety, and each of which preferably having a radius of curvature of 5 mm.

The configuration of a first alternate embodiment of the cover layer of resilient material 28 can best be seen in FIG. 3, which is an enlarged cross sectional view taken on line 3—3 of FIG. 1, illustrating a first alternate embodiment of the cover layer of the present invention with spherically-shaped magnets sitting in voids therein, and as such will be discussed with reference thereto.

The first alternate embodiment of the cover layer of resilient material 28 includes a cover layer plurality of spherically-shaped permanent magnets 32, each of which being disposed in, and not filling, a cover layer void 34 in each projection of the cover layer plurality of hemispherically-shaped projections 30 of the cover layer of resilient material 28, and contacting the core outer longitudinal surface 26 of the elongated, slender, and slightly downwardly tapering cylindrically-shaped core 20, and having a diameter of 1 mm.

The configuration of a second alternate embodiment of the cover layer of resilient material 28 can best be seen in FIG. 4, which is an enlarged cross sectional view taken on line 4—4 of FIG. 1, illustrating a second alternate embodiment of the cover layer of the present invention with square-parallelepiped-shaped magnets sitting in voids therein, and as such will be discussed with reference thereto.

The second alternate embodiment of the cover layer of resilient material 28 includes a cover layer plurality of square-parallelepiped-shaped permanent magnets 36, each of which being disposed in, and not filling, a cover layer void 38 in each projection of the cover layer plurality of hemispherically-shaped projections 30 of the cover layer of resilient material 28, and being spaced from the core outer longitudinal surface 26 of the elongated, slender, and slightly downwardly tapering cylindrically-shaped core 20.

The configuration of a third alternate embodiment of the cover layer of resilient material 28 can best be seen in FIG. 5, which is an enlarged cross sectional view taken on line 5—5 of FIG. 1, illustrating a third alternate embodiment of the cover layer of the present invention with square-parallelepiped-shaped magnets filling voids therein, and as such will be discussed with reference thereto.

The third alternate embodiment of the cover layer of resilient material 28 includes a cover layer plurality of square-parallelepiped-shaped permanent magnets 40, each of which filling a cover layer void 42 in each projection of the cover layer plurality of hemispherically-shaped projections 30 of the cover layer of resilient material 28, and not contacting the core outer longitudinal surface 26 of the elongated, slender, and slightly downwardly tapering cylindrically-shaped core 20.

It will be understood that each of the elements described above, or two or more together, may also find a useful application in other types of constructions differing from the types described above.

While the invention has been illustrated and described as embodied in a healthy golf club grip, however, it is not limited to the details shown, since it will be understood that various omissions, modifications, substitutions and changes in the forms and details of the device illustrated and its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute characteristics of the generic or specific aspects of this invention.

The invention claimed is:

1. A healthy golf club grip adaptable to a shaft of a golf club, comprising:

a) an elongated, slender, and slightly downwardly tapering cylindrically-shaped core having a wide and circular-shaped proximal end, a narrow and circular-shaped socket distal end adapted to receive the shaft of the golf club, and an outer longitudinal surface extending from said wide and circular-shaped proximal end of said elongated, slender, and slightly downwardly tapering cylindrically-shaped core to said narrow and circular-shaped socket distal end of said elongated, slender, and slightly downwardly tapering cylindrically-shaped core;

b) a cover layer of resilient material covering said outer longitudinal surface of said elongated, slender, and slightly downwardly tapering cylindrically-shaped core in its entirety; said cover layer of resilient material having a plurality of hemispherically-shaped projections extending outwardly therefrom, in close proximity to each other, and covering said cover layer of resilient material in its entirety; and c) a plurality of square-parallelepiped-shaped permanent magnets, each of which being disposed in, and not filling, a void in each projection of said plurality of hemispherically-shaped projections on said cover layer of resilient material; each magnet of said plurality of square-parallelepiped-shaped permanent magnets contacting each projection of said plurality of hemispherically-shaped projections on said cover layer of resilient material but not contacting said outer longitudinal surface of said elongated, slender, and slightly downwardly tapering cylindrically-shaped core so as to form a space therebetween.

2. The grip as defined in claim 1, wherein said cover layer of resilient material is one of rubber and fiber material.

3. The grip as defined in claim 1, wherein each projection of said plurality of hemispherically-shaped projections on said cover layer of resilient material has a radius of curvature of 5 mm.

* * * * *